United States Patent
Ahmed et al.

(10) Patent No.: US 8,061,292 B2
(45) Date of Patent: Nov. 22, 2011

(54) WETNESS INDICATING COMPOSITION

(75) Inventors: Sharf U. Ahmed, Woodbury, MN (US); Stephen G. Rippe, White Bear Lake, MN (US)

(73) Assignee: H.B. Fuller Company, St. Paul, MN (US)

( * ) Notice: Subject to any disclaimer, the term of this patent is extended or adjusted under 35 U.S.C. 154(b) by 1232 days.

(21) Appl. No.: 11/544,909

(22) Filed: Oct. 5, 2006

(65) Prior Publication Data
US 2007/0079748 A1 Apr. 12, 2007

Related U.S. Application Data

(60) Provisional application No. 60/724,032, filed on Oct. 6, 2005, provisional application No. 60/779,013, filed on Mar. 3, 2006.

(51) Int. Cl.
*G01D 21/00* (2006.01)
(52) U.S. Cl. .......... 116/206; 524/445; 604/361
(58) Field of Classification Search .......... 604/361; 116/206; 524/275, 445
See application file for complete search history.

(56) References Cited

U.S. PATENT DOCUMENTS

| | | | |
|---|---|---|---|
| 4,231,370 A | 11/1980 | Mroz et al. | |
| 4,743,238 A | 5/1988 | Colon et al. | |
| 5,089,548 A | 2/1992 | Zimmel et al. | |
| 6,458,877 B1 | 10/2002 | Ahmed et al. | |
| 6,534,572 B1 * | 3/2003 | Ahmed et al. | 524/275 |
| 6,596,918 B1 | 7/2003 | Wehrle et al. | |
| 6,653,522 B1 | 11/2003 | Blumenthal et al. | |
| 6,677,394 B1 | 1/2004 | Butterbach et al. | |
| 6,772,708 B2 | 8/2004 | Klofta et al. | |
| 6,777,708 B1 | 8/2004 | Lin et al. | |
| 6,849,672 B2 | 2/2005 | Mehawej et al. | |
| 6,904,865 B2 | 6/2005 | Klofta et al. | |
| 7,159,532 B2 | 1/2007 | Klofta et al. | |
| 2003/0125682 A1 | 7/2003 | Olson et al. | |
| 2003/0134522 A1 | 7/2003 | Onose et al. | |
| 2003/0149413 A1 | 8/2003 | Mehawej | |
| 2003/0149414 A1 | 8/2003 | Mehawej | |
| 2003/0164136 A1 * | 9/2003 | Klofta et al. | 116/206 |
| 2003/0194558 A1 | 10/2003 | Anderson | |
| 2004/0064113 A1 | 4/2004 | Erdman | |
| 2004/0191118 A1 | 9/2004 | Mody | |
| 2004/0254549 A1 | 12/2004 | Olson et al. | |
| 2005/0096428 A1 | 5/2005 | Mehawej et al. | |
| 2005/0199177 A1 | 9/2005 | Klofta et al. | |
| 2006/0293430 A1 * | 12/2006 | Wang et al. | 524/445 |

FOREIGN PATENT DOCUMENTS

| | | |
|---|---|---|
| EP | 1 043 377 A2 | 10/2000 |
| EP | 1330272 | 6/2005 |
| WO | WO 99/57201 | 11/1999 |
| WO | WO 0076443 A1 | 12/2000 |
| WO | WO 02/36177 | 5/2002 |
| WO | WO 0236177 A2 | 5/2002 |
| WO | WO 03057109 A2 | 7/2003 |
| WO | WO 03070138 A2 | 8/2003 |
| WO | WO 03070139 A2 | 8/2003 |
| WO | WO 2004028403 A2 | 4/2004 |
| WO | WO 2004084765 A2 | 10/2004 |
| WO | WO 2005004771 A1 | 1/2005 |

OTHER PUBLICATIONS

"Polyacrylates", pslc.ws/macrog/acrylate.htm, 2005.*

* cited by examiner

*Primary Examiner* — Melanie Hand
(74) *Attorney, Agent, or Firm* — Bin Su; Kirsten Stone

(57) ABSTRACT

A wetness indicating composition is disclosed that changes color in response to a change in pH. The composition comprises a water-insoluble, thermoplastic polymer composition, a superabsorbent polymer, a wetness indicator, and surfactant. The wetness indicating composition is useful in disposable absorbent articles, e.g., disposable diapers, feminine napkins, medical dressings and beddings for humans and animals.

22 Claims, No Drawings

WETNESS INDICATING COMPOSITION

CROSS REFERENCE TO RELATED APPLICATION

This application claims the benefit of the filing date of provisional application Ser. Nos. 60/724,032 filed Oct. 6, 2005 and 60/779,013 filed Mar. 3, 2006.

BACKGROUND

This invention relates to compositions capable of indicating when an absorbent product has become wet with liquids such as water, body fluids (e.g., blood, urine) and the like, articles employing such compositions, and methods of determining if an article is wet.

Absorbent articles, such as disposable diapers (including adult incontinence undergarments), feminine hygiene products (including sanitary napkins), medical dressings, bedding (both human and animal), wetness indicators used with home clothes dryer, etc. are designed to absorb and hold liquids such as water and body fluids. Often the article employs a superabsorbent polymer (SAP) to facilitate the absorption of the liquids. It is desirable to know when the absorbent articles have become wet with such liquids so that they can be changed before they leak. However, it is not always readily apparent to know when that time has come due to the protective coating layers on, and/or garments worn over, the absorbent articles. Accordingly, there remains a need to provide a mechanism by which a care giver such as a parent, nurse, day care provider, home health care aide, pet owner, etc., can easily determine if the article is wet, and if so, change it in a timely manner.

SUMMARY

The present invention is directed to compositions that indicate the presence of liquids on absorbent articles, to absorbent articles utilizing such compositions, and to methods of indicating the presence of liquids on absorbent articles using such compositions.

In one aspect, the invention comprises a wetness indicating composition that includes (a) at least one water insoluble, thermoplastic polymer composition, (b) at least one superabsorbent polymer (SAP), (c) a wetness indicator comprising an indicating agent and a pH modifier, (d) at least one surfactant, and (e) optionally at least one nanoclay powder. The nanoclay powder may have a surface comprising an organic material such as a quaternary ammonium salt.

The present invention also provides an absorbent article that employs a wetness indicating composition according to the invention.

In another aspect, the invention provides a method of indicating the presence of wetness on an absorbent article. The method comprises the steps of providing an absorbent article, applying a wetness indicating composition of the invention to at least a portion of the surface of an absorbent article, exposing the wetness indicating composition to a liquid such as water or body fluids, and determining the presence of a color change in the wetness indicating composition.

The present invention also provides precursor compositions useful in making the wetness indicating composition of the invention. These precursor compositions also have a wetness indicating capability. In one aspect, a precursor composition is provided that comprises (a) at least one super absorbent polymer (SAP), (b) a wetness indicator that includes an indicating agent and a pH modifier, and (c) optionally the nanoclay powder having a surface comprising a quaternary ammonium salt.

In another aspect, a precursor composition is provided that comprises (a) at least one water insoluble, thermoplastic polymer composition, (b) at least one wetness indicator comprising an indicating agent and a pH modifier, (c) at least one surfactant, and (d) the nanoclay powder having a surface comprising a quaternary ammonium salt.

The various aspects of the present invention provide a number of advantages. For example, the invention provides a quick color change when contacted with either water or body fluids. This allows the observer to quickly see that the absorbent article has been exposed to fluids and determine when a fresh absorbent article is needed. Additionally, the color change can be made to be vivid, thereby enhancing the visual signal and facilitating the identification of the presence of wetness in the absorbent article.

Those aspects of the invention that utilize the SAP and the water insoluble, thermoplastic polymer composition will absorb some of the liquid that they are exposed to. Even so, they retain their integrity after such exposure and remain intact. Consequently, they can be applied to any number of different locations on the absorbent article without fear of their being dissolved away. The composition of the invention may, for example, be placed at an edge of the article, such as at the leg opening of a diaper; it may be centrally located; or it may be located at multiple locations. This facilitates the ability for a caregiver to determine if the article is wet.

Those aspects of the invention that utilize the nanopowder show improved thermal and humidity stability. Thus, they are resistant to settling and/or phase separation when exposed to high temperatures (e.g., 275° F. (135° C.)) for 24 hours. Additionally, they are resistant to premature color change when exposed to heat and high humidity (e.g., 100° F. (37° C.) and 90% relative humidity) for 24 hours.

Additionally, because the compositions of the invention retain their integrity even after exposure to the liquids, the color change that occurs upon such exposure does not quickly disappear. This color change retention time gives the care giver more time to observe the color change and change the article.

DETAILED DESCRIPTION

The term "thermoplastic polymer composition" as used herein means a polymer composition that is reversibly capable of softening or fusing when heated, and hardening again when cooled.

The term "water insoluble" as used herein means an ingredient or a composition that is essentially insoluble in an aqueous environment. Such ingredients are soluble in water at a concentration of less that 1% by weight, preferably less than 0.5% by weight.

The term "body fluid" as used herein means a blood, urine, interstitial fluids, etc. These fluids are saline in nature. The term "body fluids" is used herein interchangeably with the term "saline".

The term "nanoclay powder" refers to a dry particulate clay comprising granules or platelets that have a maximum dimension of less than 100 micrometer (μm).

Thermoplastic Polymer Composition

The water insoluble, thermoplastic polymer composition used in the invention provides a binding capability to the composition. Because it is resistant to water and saline, the thermoplastic polymer composition does not noticeably degrade upon exposure to these fluids. As a result, such wetness indicating compositions do not dissolve in the presence of these fluids.

The thermoplastic polymer composition may comprise, in its entirety, a single water insoluble thermoplastic polymer or a blend of water insoluble thermoplastic polymers. Alternatively the water insoluble thermoplastic polymer composition may comprise at least one water insoluble thermoplastic polymer in combination with other thermoplastic diluents such as tackifying resins, plasticizers, waxes, and combinations thereof, and antioxidants and pigments. While the thermoplastic polymer alone may provide adequate adhesive properties to hold the wetness indicating composition in place, preferably it is combined with tackifiers, plasticizers, and waxes, etc. to modify the adhesive properties for use in the intended application. For some embodiments, a relatively high viscosity thermoplastic polymer is combined with relatively low viscosity thermoplastic components to enhance the cohesive strength of the wetness indicating composition while maintaining good processability. For this embodiment, the relatively high viscosity polymer generally has a melt index (MI) of about 400 g/10 min. or less, preferably about 200 g/10 min. or less, more preferably about 100 g/10 min. or less, and most preferably less than about 50 g/10 min.

A wide variety of thermoplastic polymers are suitable for use in the present invention. Exemplary polymers for use in the invention include styrenic block copolymers, amorphous and crystalline polyolefins including homogenous and substantially linear ethylene/alpha-olefin interpolymers; interpolymers of ethylene such as ethylene-vinyl-acetate (EVA), ethylene-methyl acrylate (EMA) and ethylene n-butyl acrylate (EnBa); and mixtures thereof.

A wide variety of block copolymers are useful in the present invention including A-B-A triblock structures, A-B diblock structures, (A-B)$_n$ radial block copolymer structures, as well as branched and grafted versions of such, wherein the A blocks are non elastomeric polymer blocks, typically comprising polystyrene, and the B blocks are unsaturated conjugated diene or hydrogenated version thereof. In general, the B block is typically isoprene, butadiene, ethyleneibutylene (hydrogenated isoprene), and mixtures thereof. Commercial embodiments include the Kraton® D and G series block copolymers, available from Shell Chemical Company (Houston, Tex.), Europrenet® Sol T block copolymers available from EniChem (Houston, Tex.), Vector® block copolymers available from Exxon (Dexco) (Houston, Tex.), as well as others. Block copolymer based compositions are particularly useful for pressure sensitive adhesive applications which generally employ a relatively low melt index block copolymer (less than 50 g/10 min) in combination with at least one tackifying resin and plasticizing oil.

Alternately, the composition may include amorphous and crystalline polyolefins including homogeneous and substantially linear ethylene/alpha-olefin interpolymers, interpolymers of ethylene such as ethylene-vinylacetate, ethylene-methyl acrylate and ethylene n-butyl acrylate, and mixtures thereof.

Amorphous polyolefins or amorphous polyalphaolefins (APAO) are homopolymers, copolymers, and terpolymers of $C_2$-$C_8$ alphaolefins. They are typically polymerized by means of processes which employ Ziegler-Natta catalysts resulting in a relatively broad molecular weight distribution. Commercially available amorphous polyalphaolefins include Rextac® and REXFlex® propylene based homopolymers, ethylene-propylene copolymers and butenepropylene copolymers available from Rexene (Dallas, Tex.) as well as Vestoplast® alpha-olefin copolymers available from Hils (Piscataway, N.J.).

Metallocene polyolefins are also useful as the water insoluble, thermoplastic polymer. These materials are homogeneous linear and substantially linear ethylene polymers prepared using single-site or metallocene catalysts. Substantially linear ethylene polymers are commercially available from Dow Chemical Company and include polyolefin plastomers available under the AFFINITY trade designation, homogeneous linear ethylene polymers are available from Exxon Chemical Company under the trade designation EXACT. Homogeneous linear and substantially linear ethylene polymers have a relatively low melt index, for example less than about 50 g/10 min.

The term "interpolymer" is used herein to indicate a copolymer, terpolymer, or higher order polymer having at least one other comonomer polymerized with ethylene. Interpolymers of ethylene are those polymers having at least one comonomer selected from the group consisting of vinyl esters of a saturated carboxylic acid wherein the acid moiety has up to 4 carbon atoms, unsaturated mono- or dicarboxylic acids of 3 to 5 carbon atoms, a salt of the unsaturated acid, esters of the unsaturated acid derived from an alcohol having 1 to 8 carbon atoms, and mixtures thereof. The melt index of the interpolymers of ethylene may range from about 50 to about 2000, from about 100 to 1500, from about 200 to 1200, and from about 400 to 1200 g/10 min.

If employed uncompounded, the ethylene to unsaturated carboxylic comonomer weight ratio is preferably greater than about 3:1, more preferably about 2:1. Hence the comonomer concentration is preferably greater than 30 wt-%, more preferably greater than 33 wt-% and most preferably greater than 35 wt-%, with respect to the total weight of the ethylene interpolymer. The melt index of the interpolymers of ethylene may range from about 50 to about 2000, preferably from about 100 to 1500, more preferably from about 200 to 1200, and most preferably from about 400 to 1200 g/10 min. When employing a polymer having too low of a melt index uncompounded, the strength of the polymer tends to constrain the swelling of the SAP particles. However, as previously discussed, the disadvantages of the lower melt index interpolymers of ethylene can be overcome by formulating the polymer with diluents.

Suitable ethylene/unsaturated carboxylic acid, salt and ester interpolymers include ethylene/vinyl acetate (EVA) ethylene/acrylic acid (EEA) and its ionomers; ethylene/methacrylic acid and its ionomers; ethylene/methyl acrylate (EMA); ethylene/ethyl acrylate; ethylene/n-butyl acrylate (EnBA); as well as various derivatives thereof that incorporate two or more comonomers.

Other thermoplastic polymers include polylactide, e.g., caprolactone polymers, and poly (hydroxy-butyrate/hydroxyvalerate), certain polyvinyl alcohols, biodegradable aliphatic aromatic copolyesters such as Eastman Copolyester 14766 (Eastman Chemical), Ecoflex® copolyester from BASF, linear saturated polyesters, examples of which are available under the trade designations DYNAPOL and DYNACOLL from Huls, poly(ethylene oxide) polyether amide and polyester ether block copolymers, examples of which are available under the trade designations PEBAX from Atochem and RITE-FLEX from Hoechst Celanese, and polyamide polymers, examples of which are available under the trade designations UNIREZ (Union Camp), VESTAMELT (Huls) and GRILTEX (EMS-Chemie). Still other useful thermoplastic polymers include the polyether/polyester polymers available under the trade designation HYTREL from Du Pont, and the biodegradable polyesters available under the trade name PLA from Cargill.

The amount of the water insoluble, thermoplastic polymer used in the present invention typically comprises from about 5% by weight to about 80% by weight of the moisture indicating composition. Preferably it comprises from about 10% by weight to about 50% by weight of the composition. More preferably, it comprises from about 10% by weight to about 30% by weight of the composition.

As previously stated, the water insoluble, thermoplastic polymer composition used in the invention preferably further comprises at least one additional ingredient. Examples of such ingredients include those that are commonly employed in hot melt adhesive compositions including plasticizers, tackifiers, waxes, and additives such as antioxidants and pigments.

Useful plasticizers are plasticizing oils such as hydrocarbon oils low in aromatic content, mineral oil (e.g., Purity 35 mineral oil from PetroCanada Lubricants (Calgary, Canada)). Preferred plasticizing oils are paraffinic or naphthenic. Examples of suitable commercially available plasticizing oils are available under the trade designations Calsol 555 from Calumet Refining Co. (Chicago, Ill.), and Nyflex 222B from Nynaf Napthenic AB (Sweden). The plasticizing oil is preferably present in the composition in an amount of from 5% by weight to about 30% by weight.

In general, the type of additional ingredient(s) will be selected to insure sufficient compatibility of the components of the water insoluble, thermoplastic polymer composition as a whole. In a preferred embodiment, the thermoplastic component of the composition of the present invention comprises at least one diluent having polar functionality. The diluent is preferably a plasticizer or wax having a molecular weight (Mw) of less than 3000 and preferably less than 2000. The diluent is preferably water insensitive, yet sufficiently polar to reduce the surface tension and/or contact angle of the thermoplastic composition relative to a comparative composition comprising the same ingredients in the absence of such ingredient. Polar diluents include plasticizers and waxes having at least one polar group per molecule. The polar group may be a terminal group or bonded to one or more units in the middle of the molecule. Polar groups include alcohol, ether, ester, epoxy, carboxylic acid, amine, amide, aldehyde, ketone, oxime, sulphonic acid, and sulfonamide groups. It is surmised that the polar diluent may plasticize the SAP. Hence, combining the SAP with polar plasticizer alone may increase the absorption rate. However, in the absence of a polymer, plasticizer alone typically could not contribute a continuous thermoplastic phase to disperse the SAP within. Preferably, the diluent is employed at an amount ranging from about 5 wt-% to about 30-wt-% and more preferably in an amount ranging from about 10 wt-% to about 20 wt-% of the total composition.

Exemplary polar plasticizers include phthalate plasticizers such as dioctyl phthalate and butyl benzyl phthalate (e.g., Santicizer 160 from Monsanto); liquid polyesters such as Dynacol 720 from Huls and liquid polymeric plasticizer available from C P. Hall; benzoate plasticizers such as 1,4-cyclohexane dimethanol dibenzoate (e.g., Benzoflez 352 from Velsicol), diethylene glycol/dipropylene glycol dibenzoate (e.g., Benzoflez 50 from Velsicol), and diethylene glycol dibenzoate where the mole fraction of hydroxyl groups which have been esterified ranges from 0.5 to 0.95 (e.g., Benzoflex 2-45 High Hydroxyl also from Velsicol); phosphite plasticizers such as t-butyl diphenyl phosphate (e.g., Santicizer 154 from Monsanto); liquid rosin derivatives having Ring and Ball softening points below about 60° C. such as methyl ester of hydrogenated rosin (e.g., Hercoyn D from Hercules); as well as vegetable and animal oils such as glycerol esters of fatty acids and polymerizable products thereof. Preferred plasticizers include esters of citric acid such as Citroflex® 2, A-2, 4, A-4, A-6, and B-6; butyl benzyl phthalate, toluene sulfonamide, benzoate plasticizers such as 1,4-cyclohexane dimethanol dibenzoate, diethylene glycol/dipropylene glycol dibenzoate, and diethylene glycol dibenzoate where the mole fraction of hydroxyl groups which have been esterified ranges from 0.5 to 0.95.

Further, water soluble or water dispersible plasticizers may also be employed, provided the presence thereof does not render the thermoplastic composition water soluble and does not impede the rate of absorption of the SAP. Suitable examples include polyethylene glycol with molecular weight below about 2000 and preferably less than 1000, derivatives of polyethylene glycol including Pycal 94, the phenyl ether of PEG available from ICI; ethoxylated bis phenol A (e.g., Macol 206 EM from PPG Industries) and dionyl phenol ethyloxylates (e.g., Surfonic DNP from Huntsman Chemical Corp.).

Exemplary polar waxes include 12-hydroxystearamide, N-(2-hydroxy ethyl 12-hydroxy stearamide (Paricin 220 and 285 from CasChem), stearamide (Kemamide S from Witco), glycerin monostearate, sorbitan monostearate, and 12-hydroxy stearic acid. Also useful in combination with the above are less polar waxes such as N,N'-ethylene-bis stearamide (Kemamide W-40 from Witco), hydrogenated castor oil (castor wax), oxidized synthetic waxes, and functionalized waxes such as oxidized polyethylene waxes (Petrolite E-1040).

Other useful plasticizers that may be employed include hydrocarbon oils, polybutene, liquid tackifying resins and liquid elastomers. Plasticizer oils are primarily hydrocarbon oils which are low in aromatic content and which are paraffinic or naphthenic in character. Plasticizer oils are preferably low in volatility, transparent and have as little color and odor as possible. The use of plasticizers in this invention also contemplates the use of olefin oligomers, low molecular weight polymers, vegetable oils and their derivatives and similar plasticizing liquids.

Waxes are usefully employed to reduce viscosity as well as increase the blocking resistance at concentrations ranging from about 2 wt-% to about 25 wt-% and preferably from about 10 wt-% to about 20 wt-%. Larger concentrations of waxes are typically avoided since waxes tend to bloom to the surface during cooling of the thermoplastic component creating a fluid impermeable barrier layer at the surface of the composition or encapsulating the SAP, thus hindering the ability of the SAP to absorb fluid. In addition to the preferred polar waxes, other useful waxes include paraffin waxes, microcrystalline waxes, Fischer-Tropsch, polyethylene and by-products of polyethylene. Also useful waxes are commercially available hydrogenated soy bean oil waxes from Archer Daniel Midland (Decatur, Ill.) under trade name ADM Vegetable wax 866970 and Stable Flake S from Cargill Incorporated (Wayzata, Minn.).

As used herein, the term "tackifier" means any of the compositions described below that are useful to impart tack to the hot melt adhesive composition. ASTM D-1878-61T defines tack as "the property of a material which enables it to form a bond of measurable strength immediately on contact with another surface".

The composition of the invention may comprise up to about 50 wt-% of a tackifying resin. Tackifying resins are preferably employed at a concentration ranging from about 5 wt-% to about 40 wt-% and more preferably from about 10 wt-% to about 20 wt-% with respect to the total weight of the composition.

Tackifying resins comprise resins derived from renewable resources such as rosin derivatives including wood rosin, tall oil and gum rosin as well as rosin esters, natural and synthetic terpenes and derivatives of such. Aliphatic, aromatic or mixed aliphatic-aromatic petroleum based tackifiers are also useful in the invention. Representative examples of useful hydrocarbon resins include alpha-methyl styrene resins, branched and unbranched $C_5$ resins, $C_9$ resins and $C_{10}$ resins, as well as styrenic and hydrogenated modifications of such. Tackifying resins range from being a liquid at 37° C. to having a ring and ball softening point of about 135° C.

As is known in the art, various other components can be added to modify the tack, color, odor, etc., of the thermoplastic composition. Additives including antioxidants such as hindered phenolics (e.g., Irganox™ 1010, Irganox™ 1076), phosphites (e.g., Irgafos™ 168), antiblock additives, pigments and fillers, can also be included in the formulations. These additives typically comprise form about 0.1 by weight to about 5% by weight of the water insoluble, thermoplastic polymer composition.

Hydrophilic fillers are a preferred class of additives, which are useful to alter the surface properties and/or increase the rate of absorption. Hydrophilic fillers include calcium carbonate, hydroxyethyl cellulose, hydroxypropyl cellulose and starch or cellulose esters, particularly the acetates. Titanium dioxide is also useful as a filler.

When present the tackifying agent is typically present at no more than 40% by weight of the water insoluble, thermoplastic polymer composition, and more preferably at no more than 30% by weight.

Super Absorbent Polymer

The SAP useful in invention comprises a water-swellable, hydrogel-forming absorbent polymer capable of absorbing large quantities of liquids such as water, body fluids (e.g., urine, blood), and the like. Additionally, the SAP is capable of retaining such absorbed fluids under moderate pressures. Typically the SAP absorbs many times its own weight in water, preferably at least 50 times, more preferably at least 100 times, most preferably at least 150 times its weight in water. Additionally, the SAP exhibits good saline fluid absorption under load and high saline fluid absorption capacity. Typically the SAP absorbs at least 10 times, preferably at least 30 times, more preferably at least 50 times its weight in saline fluid. Even though the SAP is capable of absorbing many times its own weight in water and/or saline, it does not dissolve in these fluids.

The ability of the SAP to absorb water and/or saline fluid is related to the degree of crosslinking present in the SAP. Increasing the degree of crosslinking increases the SAP's total fluid holding capacity under load. The degree of crosslinking is preferably optimized to obtain a composition in which the rate and amount of absorbency are optimized. Preferred SAPs are at least 10%, more preferably from about 10% to about 50%, most preferably from about 20% to 40% crosslinked. Examples of suitable SAPs include crosslinked and polymerized α,β-beta ethylenically unsaturated mono- and dicarboxylic acids and acid anhydride monomers including, e.g., acrylic acid, methacrylic acid, crotonic acid, maleic acid/anhydride, itaconic acid, fumaric acid, and combinations thereof.

Superabsorbent polymers useful in the invention include, e.g., crosslinked acrylate polymers, crosslinked products of vinyl alcohol-acrylate copolymers, crosslinked products of polyvinyl alcohols grafted with maleic anhydride, crosslinked products of acrylate-methacrylate copolymers, crosslinked saponification products of methyl acrylate-vinyl acetate copolymers, crosslinked products of starch acrylate graft copolymers, crosslinked saponification products of starch acrylonitrile graft copolymers, crosslinked products of carboxymethyl cellulose polymers and crosslinked products of isobutylene-maleic anhydride copolymers, and combinations thereof.

The superabsorbent particles preferably are spherical and have an average particle size of from about 1 micrometer (μm) to about 400 (μm). Preferably the particles have an average particle size of from about 20 μm to about 200 μm, and more preferably from 20 μm to 100 μm.

Useful commercially available superabsorbent particles include, e.g., sodium polyacrylate superabsorbent particles available under the AQUA KEEP series of trade designations including, e.g., particles having an average particle size of from about 20 μm to about 30 μm available under the trade designation AQUA KEEP 10SH-NF, particles having an average particle size of from 200 μm to 300 μm available under the trade designation AQUA KEEP 10SH-P, particles having an average particle size of from 320 μm to 370 μm available under the trade designation AQUA KEEP SA60S, particles having an average particle size of from 350 μm to 390 μm available under the trade designations AQUA KEEP SA60SX, SA55SX II and SA 60SL II, and particles having an average particle size of from 250 μm to 350 μm available under the trade designation AQUA KEEP SA60N TYPE II from Sumitomo Seika Chemicals Col, Ltd. (Japan). Also available superabsorbent materials are Luquasorb 1010 and Luquasorb 1003 from BASF, Ludwigshafen, Germany.

The wetness indicating compositions of the invention employ an amount of the SAP adequate to absorb an adequate level of the liquid to cause wetness indicator, described hereinafter, to change color. Useful levels of SAP comprise at least about 2% by weight of the wetness indicating composition. Typically, the SAP comprises from about 2% to about 50% by weight of the wetness indicating composition. Preferably, the SAP comprises from about 2% to about 30% by weight of the wetness indicating composition. More preferably, the SAP comprises from about 2% by weight to about 15% by weight of the wetness indicating composition.

Wetness Indicator

The wetness indicator used in the invention comprises an indicating agent and a pH modifier. The wetness indicator changes color in response to a change in pH thereby demonstrating the presence of, for example, water or saline. Acid-base wetness indicators are preferred because they change the color rapidly. Preferred indicators are those that change to a bright, vivid color.

Examples of useful indicating agents include Ethyl Red, Bromophenol Blue, Bromocresol Green, a mixture of Bromophenol Blue with Bromocresol Green, etc.

The pH modifier used in the wetness indicator adjusts the pH of the wetness indicator to a level sufficient to prevent it from changing color prior to being contacted with a fluid. Examples of useful pH modifiers include acidic compounds having carboxylic acid functional groups. These include, but are not limited to, isostearic, azelaic, stearic, oleaic, linoleac, ricinoleac, benzoic, citric and dimer acid groups. Optionally, inorganic acids may be added to adjust the pH. The amount of pH modifier used is sufficient to adjust the pH of the wetness indicator to a desired level.

The level of wetness indicator used in the invention is sufficient to provide a easily recognized color change when it is exposed to a fluid. For example, a useful level of the wetness indicator typically comprises from about 0.01% to about 60% by weight of the total weight of the wetness indicating composition. Preferably it is in the range of from about 0.1% by weight to 50% by weight, more preferably from about 5% to 50% by weight, of the total composition.

Surfacant

The surfactant used in the invention reduces the surface tension and/or contact angle of the thermoplastic component. Surfactants are useful in amounts ranging from about 0.5 wt-% to about 50 wt-% and preferably from about 5 wt-% to about 25 wt-% with respect to the total weight of the thermoplastic component. Suitable surfactants include non-ionic, anionic, and silicone surfactants. Exemplary non-ionic surfactants are: Ethoxylates of (i) $C_1$-$C_{18}$, preferred $C_8$-$C_9$ alkyl or dialkyl phenols, such as those sold under the tradenames Macol DNP-10, available from PPG Industries, Gurnee, Ill., a 10 mole ethoxylate of dinonyl phenol, and Triton X-100, available from Union Carbide, a 10 mile ethoxylate of octyle phenol; (ii) alkyl $C_8$-$C_{60}$ mono-alcohols such as those sold under the tradenames Surfonic L-12-8, an 8 mole ethoxylate of dodecanol, available from Huntsman Chemical Co., and Unithox 480, a 38 mole ethoxylate crystalline surfactant available from Petrolite Specialty Polymers Group, Tulsa, Okla.; and (iii) propylene oxide polymers, such as those sold under the tradename Pluronic, which are ethylene oxide/propylene oxide block copolymers having Mn of 200 to 3000, available from BASF; and benzoates formed by partial condensation of benzoic acid with hydrophilic di or mono-ols having less than 1000 Mn, such as the product of condensing about three equivalents of benzoic acid with four equivalent of diethylene glycol, commercially available as XP 1010 from Velsicol Chemical. A preferred non-ionic surfactant blend is Atmer 685, available from ICI Surfactants (Wilmington, Del.).

Suitable anionic surfactants are: $C_8$-$C_{60}$ alkyl ethoxylate sulfonates, $(CH_3-(CH_3-(CH_2)_{11-14}-(O-CH_2-CH_2)_3-SO_3^{31}\ Na^{30}$, such as, Avenel S30, available from PPG Industries; alkyl C8-C60 sulfonates, such as, Rhodapon UB ($C_{12}$—$SO_3^-Na^+$) available from Rhone Poulenc; and alkyl/aromatic sulfonates, such as those sold under the tradename Calsoft.

Suitable silicone surfactants are ethoxylates or propoxylates of polydimethyl siloxane, having a number average molecular weight of 500 to 10,000, preferably 600 to 6000, such as are sold under the tradenames Silwet L-77, L-7605, and L-7500 available from Osi Specialties, Danbury, Conn.; and product 193 from Dow Corning.

Still other suitable commercially available surfactants include Aerosol OT 100 and Aerosol OT B (dioctyl ester of sodium sulfosuccinic acid) from Cytec Industries (West Patterson, N.J.) and Rhodacal DS 10 (sodium dodecyl benzene sulfonate) from Rhone Poulenc (Cranberry, N.J.).

Nanoclay Powder

The nanoclay powder useful in the invention comprises a dry granular composition comprising granules or platelets of clays that have a maximum dimension of 100 μm. Preferably, they are derived from clays that have a maximum dimension of 200 nanometers (nm). The preferred nanoclay powders useful in the invention comprise clusters of individual platelets of the clays. The individual platelets separate from one another when contacted with a swelling agent such as water.

Nanoclay powders useful in the invention include the kaolinites, the montmorillonites/smectites, the illites, the chlorites, and combinations thereof. Preferred nanoclay powders include the montmorillonites/smectites with the montmorillonites being the more preferred nanoclay powders. The montmorillonites are magnesium aluminum silicate-containing materials.

Preferred nanoclay powders also comprise high aspect ratio platelets derived from the above-identified clays. As used herein, aspect ratio means the ratio of the length to the width of the platelets. Typically, the nanoclay powders have an aspect ratio of at least 50.

Nanoclay powders useful in the invention include synthetic layered smectites that resemble the natural clay hectorite in structure and composition. Commercially available materials of this type include the Laponite® brand nanoclay powders available from the Southern Clay Products Division of Rockwood Specialties, Inc. The Laponite® powders are prepared by combining salts of sodium, magnesium and lithium with sodium silicate at controlled rates and temperatures followed by partially crystallizing the resulting amorphous precipitate. The Laponite® nanoclay powders typically are about 0.9 nm thick and have a length of about 25 nm.

Nanoclay powders useful in the invention also include layered magnesium aluminum silicates. These materials are also sometimes referred to as montmorillonites.

The surface of the nanoclay powder may comprise an organic material. Quaternary ammonium salts are one class of organic materials that may be used on the surface of the nanoclay powder.

Quaternary ammonium salts useful on the surface of the nanoclay powder include, but are not limited to, dimethyl benzyl, hydrogenated tallow quaternary ammonium (2 MBHT); dimethyl, dihydrogenated tallow quaternary ammonium (2M2HT); dimethyl dihydrogenated tallow, 2-ethylhexyl quaternary ammonium (2 MHTL8); methyl, tallow, bis-2-hydroxyethyl, quaternary ammonium (MT2EtOH); and combinations thereof.

Commercially available nanoclay powders that are useful in the invention and that employ a quaternary ammonium salt on the surface include Cloisite® 10A, 15A, 20A, 25A and 30B from the Southern Clay Products Division of Rockwood Specialties, Inc. These are natural montmorillonites whose surface comprises a quaternary ammonium salt. The platelets are about 1 nm thick and from about 70 to 150 nm across.

Cloisite® 10A employs dimethyl, benzyl, hydrogenated tallow, quaternary ammonium (2 MBHT) as the quaternary ammonium modifier. Cloisite® 15A and Cloisite® 20A employ dimethyl, dihydrogenated tallow, quaternary ammonium (2M2HT), as the quaternary ammonium modifier. Cloisite® 25A employs dimethyl, dihydrogenated tallow, 2-ethylhexyl quaternary ammonium (2 MHTL8) as the quaternary ammonium modifier. Cloisite® 30B employs methyl, tall, bis-2-hydroxyethyl, quaternary ammonium (MT2EtOH) as the quaternary ammonium modifier. These materials have typical dry particle sizes (by volume) of 10% less than 2μ, 50% less than 6μ and 90% less than 13μ. The hydrogenated tallow used in these quaternary ammonium salts comprises about 65% by weight $C_{18}$, about 30% by weight $C_{16}$ and about 5% by weight $C_{14}$.

These nanoclay powders comprise up to about 5% by weight of the wetness indicating composition. Typically, it comprises from about 0.3 to about 5% by weight of the wetness indicating composition. Preferably, it comprises from about 0.5 to about 1% by weight of the wetness indicating composition.

The wetness indicating composition of the invention may be made by, for example, combining all of the ingredients together in a suitable vessel and then mixing them under heat (e.g., 150-175° C.) until a uniform composition is obtained. When the composition utilizes the hot melt adhesive the composition may be prepared by melting and blending all of the ingredients of the adhesive together followed by adding the SAP to the molten hot melt adhesive. The remaining ingredients may then be added to the molten composition. The molten wetness indicating composition may be palletized, pillowed, or cast into molds or drums, etc., for subsequent remelting and application.

The composition of the present invention may be applied by a variety of methods. These include any hot melt application technique such as slot coating, spiral spraying, screen printing, foaming, engraved roller or meltblown adhesive application techniques. Additionally, it may be applied by digital printing techniques. The inventive composition may be present as a stripe, a coating, or film layer on at least one substrate or as a portion of an article. When applied as a stripe, the composition may be a straight line, a curved line, or a spiral line (e.g., one that crosses back and forth over itself. Additionally, the composition may be applied in a discontinuous manner. Thus the stripe may comprise one or more separate segments. The composition may also be applied in a series of dots on a substrate. The composition of the invention may also be provided as a film or sheet.

The wetness indicating composition of the present invention is useful for a variety of end-uses, particularly those such as disposable absorbent articles such as disposable diapers, feminine napkins, medical dressings, beddings for humans and animals, etc. Accordingly, the thermoplastic composition may be applied to a variety of substrates using any suitable method, particularly the hot melt adhesive application techniques described above.

The invention is further illustrated by the following non-limiting examples. All composition exemplified are expressed in parts by weight unless noted otherwise.

EXAMPLES 1-7

General Preparation

A series of wetness indicating compositions according to the invention were prepared. A premix composition having the water insoluble, thermoplastic polymer composition, the super absorbent polymer, and the surfactant was prepared. A blend of stearic acid and the indicating agent was then prepared to form the wetness indicator. This was then combined with the premix composition to form the wetness indicating compositions.

|  | Premix Composition | |
| --- | --- | --- |
|  | A | B |
| Wingtack 86[1] | 28.5 |  |
| Sylvarez ZT5100[2] | 19.4 |  |
| Benzoflex 352[3] | 12.5 |  |
| Nyflex 222B[4] | 15.0 |  |
| Vector 4211[5] | 22.3 |  |
| Irganox 1010[6] | 0.3 |  |
| Rhodacal DS10[7] |  | 6 |
| SAP[8] |  | 45 |
| HL-1500X[9] |  | 49 |

| Wetness Indicating Compositions | | | | | | | |
| --- | --- | --- | --- | --- | --- | --- | --- |
| RM | Ex. 1 | Ex. 2 | Ex. 3 | Ex. 4 | Ex. 5 | Ex. 6 | Ex. 7 |
| Premix A | 65.6 | 66 |  |  |  | 67.5 |  |
| Premix B |  |  | 40 |  |  |  |  |
| Rhodacal DS10[7] | 8 | 12 |  |  | 22.4 | 10 | 10 |
| SAP[8] | 6.4 | 2 |  |  | 6.4 | 2 | 2 |
| Stearic Acid | 19.9 | 19.9 | 10 | 8 | 39.8 | 19.8 | 19.8 |
| Bromocresol green | 0.1 | 0.1 | 0.05 | 0.05 | 0.2 | 0.2 | 0.2 |
| NW1078A[10] |  |  |  | 42 |  |  |  |
| HL-8150XZP[11] |  |  |  |  | 131.2 |  |  |
| HL-1696XZP[12] |  |  |  |  |  |  | 67.5 |
| Cloisite 10A[13] |  |  |  |  |  | 0.5 | 0.5 |

[1]Wingtack 86 is a modified C5 Petroleum hydrocarbon resin available from Goodyear Tire and Rubber Company, Akron, Ohio.
[2]Sylvarez ZT5100 is a tackifying resin available from Arizona Chemicals, Jacksonville Florida.
[3]Benzoflex 352 is a benzoate plasticizer available from Velsicol of Rosemount, Illinois.
[4]Nyflex 222B is a processing oil available from Nynas Naphthenics A B, Stockholm, Sweden.
[5]Vector 4211 is a Styrenic block copolymer available from Dexco Polymers, Houston, Texas..
[6]Irganox 1010 is a hindered phenol antioxidant available from Ciba Geigy, Hawthorne, New York.
[7]Rhodacal DS10 is sodium dodecylbenzene sulfonide from Rhone Poulenc, Cranberry, New Jersey.
[8]AQUA KEEP 10SHNF20 is a sodium polyacrylate superabsorbent polymer available from Sumitomo Seika Chemicals Co., Ltd. (Japan).
[9]HL-1500X is a Styrenic Block copolymer based adhesive available from H. B. Fuller Company, St. Paul, MN
[10]NW1078A is an absorbent hotmelt from block copolymer/SAP polymer blend available from H. B. Fuller Co., St. Paul., MN.
[11]HL-8150XZP is a styrenic Block copolymer based adhesive available from H. B. Fuller Company, St. Paul, MN
[12]HL-1696XZP is a styrenic block copolymer based adhesive system available from H. B. Fuller Company, St. Paul, MN.
[13]Cloisite 10A is a surface modified nanoclay available from Southern Clay Products Division of Rockwood Specialties, Inc.

Preparation of Premix Compositions

All ingredients are measured in an aluminum can and heated in the oven at 160-175° C. until most of the raw materials are melted. The can is then placed in a heating mantle and the contents are stirred for at least 1.5-2 hour until a smooth homogeneous mixture is obtained.

For larger scale samples, RM's are mixed in a sigma mixer at 160-175° C. until a smooth homogeneous mixture is obtained.

Preparation of Wetness Indicating Compositions

To molten (140-150° C.) Premix (Examples 1-6) or to molten HL-1696XZP (Example 7) the SAP was added in a portion wise manner with stirring until the mixture is smooth. Rhodacal DS 10 was then added and stirred until it was well mixed. Stearic acid was then added and stirred until smooth. This mixture was then stirred for additional 15 minutes at this temperature. Indicator agent (Bromocresol green) was then added and mixed for 15 minutes at this temperature. Films were drawn on release paper using a draw down bar to a 1 mil thickness (25 μm).

In some cases a premix including the SAP and Rhodacal DS 10 was used. In this case the Premix B is melted and then the stearic acid was added and mixed until smooth. The indicator agent was then added and mixed for 15 minutes. Films were drawn as described above.

In all cases the applied films had a yellow color.

Testing:

Color Change

To a portion of the film 2.5 ml of water or saline is added. The time to color change and the actual color change were observed and noted.

The results of the tests are given below.

| Example | Liquid | Time to Color Change | Color Change |
|---|---|---|---|
| 1 | Water | Immediate | Yellow to blue |
|   | Saline | 5 seconds | Yellow to greenish blue |
| 2 | Water | Immediate | Yellow to blue |
|   | Saline | 5 seconds | Yellow to greenish blue |
| 3 | Water | Immediate | Yellow to blue |
|   | Saline | 5 seconds | Yellow to greenish blue |
| 4 | Water | Immediate | Yellow to blue |
|   | Saline | 5 seconds | Yellow to greenish blue |
| 5 | Water | Immediate | Yellow to blue |
|   | Saline | 5 seconds | Yellow to greenish blue |
| 6 | Saline | <5 seconds | Yellow to blue |
| 7 | Saline | 5 seconds | Yellow to blue |

The saline employed in these tests was a solution of 0.9% NaCl in distilled water.

Humidity Resistance

Commercially available diapers containing commercially available wetness indicator stripes were cut into 4 inch (10 cm)×6 (15 cm) inch size pieces. Strips (sample size and dimension as of the existing stripes in the diaper) of lab made samples or competitive samples were then placed within 1 cm of the existing stripes. All sides were then closed using a clear packaging tape such as Scotch® Brand 373. The resulting prototype diapers were then placed in a humidity chamber maintained at 100 F. (37° C.)/90% Relative Humidity for approximately 24 hours. Samples were checked periodically for any color change.

The results of the humidity tests are given below.

|  | 24 Hour Humidity Test |
|---|---|
| Commerical Diaper 1 | |
| Existing Yellow Wetness Indicator | Color change to blue in <10 hours |
| Wetness Indicator of Ex. 7 | No color change |
| Commercial Diaper 2 | |
| Existing Yellow Wetness Indicator | Color change to blue in <10 hours |
| Wetness Indicator of Ex. 6 | No color change |
| Wetness Indicator of Ex. 7 | No color change |

Thermal Stability

A sample (100 g) of the wetness indicating composition of the invention was placed in a glass container and put in an oven at 275° F. (135° C.) for 24 hours and periodically checked for separation or for the formation of solids at the bottom. The results are given below.

| Wetness Indicating Compositions | Observation |
|---|---|
| Ex. 2 | Precipitate noted at 8 hours |
| Ex. 6 | No precipitate or separation after 24 hours |
| Ex. 7 | No precipitate or separation after 24 hours |

What is claimed is:

1. A wetness indicating composition comprising:
   (a) at least one water insoluble, thermoplastic polymer composition;
   (b) at least one surfactant;
   (c) at least one wetness indicator comprising an indicating agent and a pH modifier; and
   (d) at least one superabsorbent polymer.

2. The wetness indicating composition of claim 1 wherein the indicating agent changes color in response to a change in the pH of the wetness indicating composition.

3. The wetness indicating composition of claim 1 wherein the wetness indicator comprises from about 0.01% by weight to about 60% by weight of the wetness indicating composition.

4. The wetness indicating composition of claim 3 wherein the wetness indicator comprises from about 5% by weight to about 50% by weight of the wetness indicating composition of a pH modifier and from about 0.01% by weight to about 5% by weight of the wetness indicating composition of a wetness indicator.

5. The wetness indicating composition according to claim 1 comprising from about 5% by weight to about 80% by weight of the water insoluble, thermoplastic polymer composition; from about 0.5% by weight to about 50% by weight of the surfactant; from about 0.01% by weight to about 60% by weight of the wetness indicator, and from about 2% by weight to about 50% by weight of the super absorbent polymer.

6. The wetness indicating composition of claim 1 wherein the water insoluble, thermoplastic polymer composition further comprises at least one material selected form the group consisting of tackifying agents and plasticizers.

7. The wetness indicating composition according to claim 6 wherein at least one of the tackifying agent and the plasticizer is polar.

8. The wetness indicating composition of claim 6 comprising from about 5% by weight to about 50% by weight of the tackifying agent and from about 5% by weight to about 50% by weight of the plasticizer.

9. The wetness indicating composition of claim 1 wherein the super absorbent polymer has a particle size of from about 1 μm to about 400 μm.

10. A disposable absorbent article comprising the composition of claim 1 applied to at least a portion of a surface of a substrate.

11. The disposable absorbent article according to claim 10 selected from the group consisting of a diaper, a feminine napkin, a medical dressing and beddings for humans and animals.

12. A wetness indicating composition comprising at least one superabsorbent polymer and a wetness indicator, said wetness indicator comprising an indicating agent and a pH modifier.

13. A wetness indicating composition comprising:
   (a) at least one water insoluble, thermoplastic hot melt polymer composition;
   (b) at least one surfactant;
   (c) at least one wetness indicator comprising an indicating agent and a pH modifier; and
   (d) at least one superabsorbent polymer.

14. A method of making a wetness indicating composition according to claim 1, the method comprising the steps of:
   (a) combining the water insoluble, thermoplastic polymer, the superabsorbent polymer in a suitable mixing device and heating until the combination has become molten;
   (b) adding the surfactant, and optionally a nanoclay powder, to the molten mixture and mixing until a uniform molten mixture is obtained;
   (c) subsequently adding the wetness indicator to the uniform molten mixture and mixing for a time to provide a uniform molten mixture of the wetness indicating composition; and
   (d) optionally, solidifying the mixture of step (c).

15. The wetness indicating composition according to claim 1 further comprising a nanoclay powder.

16. The wetness indicating composition according to claim 15 wherein the nanoclay powder is selected from the group consisting of kaolinites, montmorillonite/smectites, illites, chlorites and combinations thereof.

17. The wetness indicating composition according to claim 15 wherein the surface of the nanoclay powder comprises a quaternary ammonium salt that has a cation selected from the group consisting of (a) dimethyl, benzyl, hydrogenated tallow quaternary ammonium (2 MBHT), (b) dimethyl, dihydrogenated tallow, quaternary ammonium (2M2HT), (c) dimethyl, hydrogenated tallow, 2-ethylhexyl quaternary ammonium (2 MHTL8), (d) methyl, tallow, bis-2-hydroxyethyl, quaternary ammonium (MT2EtOH), and (f) combinations thereof.

18. The wetness indicating according to claim 15 wherein the nanoclay powder comprises from about 0.3% by weight to about 5% by weight of wetness indicating composition.

19. The wetness indicating composition according to claim 15 wherein the nanoclay powder comprises platelets.

20. The wetness indicating composition according to claim 19 wherein the individual platelets of the nanoclay powder have an aspect ratio of at least 50.

21. The wetness indicating composition according to claim 15 wherein the nanoclay powder has a dry particle size of less than 15 micrometers by volume.

22. The wetness indicating composition according to claim 1, further comprising nanoclay powder free from quaternary ammonium salt on its surface.

* * * * *